United States Patent [19]

Burton et al.

[11] 4,082,733

[45] Apr. 4, 1978

[54] BLOCKING PROTEIN FRACTION RECOVERY METHOD AND PRODUCT

[75] Inventors: Lawrence Burton, Commack; Frank Friedman, New York, both of N.Y.

[73] Assignee: Immunology Research Foundation, Inc., Great Neck, N.Y.

[21] Appl. No.: 600,028

[22] Filed: Jul. 29, 1975

[51] Int. Cl.² ............................................... A23J 1/06
[52] U.S. Cl. ............................ 260/112 B; 23/258.5 R; 210/DIG. 23
[58] Field of Search ........................ 260/112 R, 112 B; 23/258.5 R; 210/DIG. 23

[56] References Cited

U.S. PATENT DOCUMENTS

| | | | |
|---|---|---|---|
| 2,710,293 | 7/1955 | Gerlough | 260/112 B |
| 2,710,294 | 7/1955 | Gerlough | 260/112 B |
| 3,003,918 | 10/1961 | Sanders | 260/112 B |
| 3,657,116 | 4/1972 | Haller | 210/DIG. 23 |
| 3,677,710 | 7/1972 | Hirsch | 23/258.5 R |
| 3,864,089 | 2/1975 | Tiffany | 23/258.5 R |
| 3,957,654 | 5/1976 | Ayres | 23/258.5 R |

OTHER PUBLICATIONS

Karlson, "Introduction to Modern Biochemistry", Academic Press, New York, 1968, pp. 62–69.

*Primary Examiner*—Paul R. Michl
*Attorney, Agent, or Firm*—Barry Kramer

[57] ABSTRACT

A process is provided for the isolation of a protein fraction herein termed the "blocking protein fraction" or "BPF", from mammalian blood. The process comprises a series of centrifugal separations of blood fractions under conditions which maintain the integrity of the desired material as it existed in vivo.

The blocking protein fraction, is a new material and it constitutes another aspect of the disclosure. Isolated BPF, a natural protein or a derivative thereof, is useful to prevent tissue implant rejection, and as standard from the determination of the tumor remission activity of other materials isolated from blood.

7 Claims, No Drawings

BLOCKING PROTEIN FRACTION RECOVERY METHOD AND PRODUCT

RELATED APPLICATIONS

Applicants are filing concurrently herewith several applications relating to the present invention and identified by their titles which are as follows:

1. Deblocking Protein Fraction Recovery Method And Product, Ser. No. 600,026 filed July 29, 1975; and
2. Tumor Complement Fraction Recovery Method And Product, Ser. No. 600,027 filed July 29, 1975.

FIELD OF THE INVENTION

The present invention relates to a method for isolating a specific fraction of mammalian blood. It relates further to the provision of a composition which can be administered to prevent tissue implant rejection. It relates still further to the use of said fraction to determine the tumor remission activity of other substances isolated from blood.

The inventors have published the following articles, relating to the field of this invention:

1. Annals of The New York Academy of Sciences, Vol. 100, Part II, pages 791–814 (1963)
2. Pigment Cell Biology, pages 279–299, Academic Press, 1959
3. Transactions of The New York Academy of Sciences, Ser. II, Vol. 25, pages 29–32 (Nov. 1962)

BACKGROUND OF THE INVENTION

In the related applications filed concurrently herewith and referred to above, applicants disclose several inventions relating to tumor remission and prevention in mammals. One aspect of these inventions is the fractionation, remission and prevention of tumors. These inventions arose, in part, as a result of the assumption that the body has within it an anticancer immune defense mechanism which prevents or controls the formation of tumor cells, and that tumors arise only when this system does not function properly or sufficiently, either due to an imbalance which may be genetic in origin, or the presence of more cancer producing stress than the animal's system can handle.

Based upon the foregoing, applicants proceeded to fractionate mammalian blood. Since the materials sought were unknown in structure, the properties vis a vis their effect on the animal, had to be determined empirically. For example, if a fraction of the animal's blood is injected into a tumor bearing mouse and the tumor does not respond, then the blood may be centrifuged to give a sediment and a supernatant, each of which is again tested on the mice. If again the tumors do not respond, then perhaps the blood fraction is centrifuged at a higher speed and the resultant materials are again tested. If it turns out that the resultant sediment causes a positive anti-tumor response, then it is clear that centrifuging at the higher speed resulted in the separation of a tumor-controlling component. Also considered was the presence of a material in the supernatant which, before being separated from the active sediment, inhibited the tumor activity of the material in the sediment.

Proceeding in the foregoing fashion, the Applicants were able to isolate three blood components or fractions, the presence in balanced proportion of which, both inhibit the formation and cause necrosis of neoplasmic tissue. These components are virtually non-toxic and have no apparent side effects or adverse effect on normal tissue. The toxicity is so minimal that an L.D. 50 has thus far not been obtainable.

As stated in the above-referred to concurrently filed applications, though the chemical structure of these components has not been illlucidated, the materials have been identified and named as follows:

1. Tumor Complement Fraction ("TCF")
  a peptide chain or derivative thereof that attacks the tumor and causes necrosis of the tumor tissue
2. Blocking Protein Fraction ("BPF")
  a substance that blocks the activity of TCF
3. De-Blocking Protein Fraction ("DPF")
  a protein or derivative thereof that neutralizes or "de-blocks" BPF TCF, BPF and DPF must be in balance to maintain a tumor free condition. In a normal animal, tumor growth is prevented by the presence of a greater amount of TCF than BPF, there being generally seven units of TCF for each unit of DPF. In a tumor-bearing animal, less TCF is present in the blood. By administering DPF to a tumor-bearing animal, it is theorized that TCF which is bound to the BPF, can be freed again to do its work of killing tumor cells. If TCF is added along with DPF, the necrosis of tumor tissue can be made to proceed at a more rapid rate. Thus, the essence of tumor treatment according to the principles stated in the above-referred to applications, is to administer TCF and/or DPF to thereby provide free TCF capable of necrosizing the tumorous tissue.

As a collorary to the foregoing conclusions, it was concluded that BPF has an inactivating effect on the body's immune defense system and can be used to prevent tissue implant rejection and it has been found that this is the case.

BPF is also useful in assaying the activity of TCF and DPF which, as disclosed in the above-referred to concurrently filed pending applications, are useful in effecting necrosis of tumor tissue.

Accordingly, it is one object of the present invention to provide a method of extracting BPF from mammalian blood without significantly altering or modifying the material from its in vivo condition.

It is a further object of the present invention to provide a mammalian blood component which tends to inactivate the body's immune defense system thereby reducing the tendency of the body to reject tissue implants.

It is a still further object of the present invention to provide a material which can be used to assay the anti-tumor activity of TCF and DPF.

PREFERRED EMBODIMENTS

The following Table shows the steps which can be employed to isolate BPF from mammalian blood.

TABLE

ISOLATION OF BPF

| Step No. | Table |
|---|---|
| 1 | whole blood + buffer |
|  |     mix and centrifuge |
|  | sediment    supernatant fluid |
| 2 |  |
|  |     centrifuge |
|  | sediment    supernatant fluid |

TABLE-continued

ISOLATION OF BPF

| Step No. | Table |
|---|---|
| 3 | |
| 4 | |

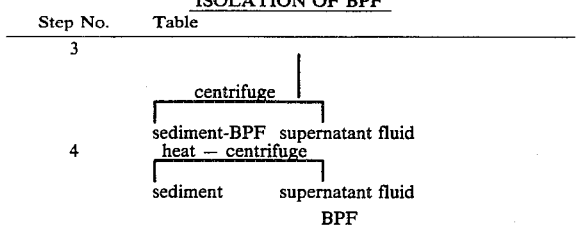

BPF is obtained by fractionating mammalian whole blood. A sample of whole blood is thoroughly mixed with a buffer solution at near neutral pH such as KH$_2$PO$_4$ (0.05M) titrated to pH 7.5 with Na$_2$HPO$_4$ (0.05M) at 42° C. The amount of buffer relative to whole blood is not critical, but preferably 0.1ml of whole blood is admixed with 2.0ml of buffer. The buffer solution is centrifuged at 5400 to 10,000g, preferably 6500g, for several minutes (e.g., 5 minutes). In Step 2, the resultant supernatant fluid is again centrifuged under the same conditions. The sediment is discarded and the supernatant fluid is again centrifuged, but this time at between 20,000 and 25,000g, preferably, 23,500g for about 15 minutes. The resultant sediment is BPF and it may be resuspended with 1.5ml of an alkaline buffer such as Na$_2$HPO$_4$ (0.05M, pH 9.2).

The BPF obtained above can be further purified, if desired, (Step 4) by heating the solution to at least 55° C. for about 10 minutes and then centrifuging at between about 20,000 and 25,000g (preferably 23,500g) for about 15 minutes. The resultant supernatant is believed to be pure BPF.

To determine the concentration of BPF isolated from 0.1ml of whole blood, the resultant supernatant fluid is analyzed in a Beckmann ACTA V spectrophotometer. Since BPF does not have a peak absorption at a wave length in the far U.V. range, that is within the capability of this model spectrophotometer, measurements of sample "cut-off" were used as quantitative indicators. Usually the term "cut-off" is used in reference to a solvent, but it can be applied to anything that has a wave length of maximum absorption near or below the instruments lower wave length limit. The strict definition of "cut-off" is the wave length at which the absorbance in a one centimeter cell is equal to 1.0. For measurement of BPF, at a 0.5 centimeter cell is used in order to perform more effectively with minimal volumes at the lower wave length and to determine the wave length at which the absorbance is 0.5. When the read-out display of the Beckmann ACTA V for any sample indicates 0.5 absorbance, the wave length is referred to a BPF assay curve. This curve is constructed experimentally by serial dilutions of more than 400 samples of BPF. In this linear assay curve, starting at 197nm, each 1.0nm increase is equivalent to an increment of 3.2 units of BPF.

Preliminary investigations have indicated that BPF is a peptide. Analysis of BPF isolated from large batches of blood (200 - 200 milliliters) indicated that BPF is proteinaceous.

BPF has utility as a standard against which activity of TCF and DPF can be measured. The means for using BPF for this purpose are disclosed in the above referred to concurrently filed applications. Further, BPF is useful to prevent rejection of tissue implants. Subcutaneous or intramuscular administration of BPF tends to prevent the rejection of implanted tissue as a result of the body's IDMC. The amount of BPF to be administered depends upon the amount of unassociated BPF in the subject's blood. This can be determined by the assay methods disclosed in the above-referred to concurrently filed applications. Usually, the amount of BPF to be administered should be such that after administration, the total amount of BPF in the blood exceeds one unit for each seven units of TCF in the blood.

What is claimed is:

1. A process for the isolation of BPF which comprises:
   (a) suspending whole blood in a buffer solution of nearly neutral pH
   (b) centrifuging the whole blood suspension at 5400-10,000g to obtain a first supernatant
   (c) centrifuging the first supernatant at 20,000 to 25,000g to give a BPF sediment
   (d) optionally purifying the BPF sediment by resuspending it in an alkaline buffer and centrifuging at 20,000-25,000g to give a supernatant containing relatively pure BPF.

2. The process of claim 1 wherein the centrifuging of step (b) is conducted at 6500g.

3. The process of claim 1 wherein the centrifuging of step (c) is conducted at 23,500g.

4. The process of claim 1 wherein the centrifuging of step (d) is conducted at 23,500g.

5. A process for the isolation of BPF comprising
   (a) suspending whole blood in a nearly neutral buffer solution
   (b) centrifuging the whole blood suspension at 6500g to obtain a first supernatant
   (c) centrifuging the first supernatant at 23,500g to give a BPF sediment
   (d) optionally resuspending said BPF sediment in an alkaline buffer and centrifuging at 23,500g to give a supernatant containing relatively pure BPF.

6. The isolated product by the process of claim 1.

7. The isolated product by the process of claim 5.

* * * * *